United States Patent
Huang

(10) Patent No.: US 7,948,624 B2
(45) Date of Patent: May 24, 2011

(54) PHOTOCATALYSIS TESTING DEVICE

(75) Inventor: Chien-Hao Huang, Taipei Hsien (TW)

(73) Assignee: Hon Hai Precision Industry Co., Ltd., Tu-Cheng, New Taipei (TW)

( * ) Notice: Subject to any disclaimer, the term of this patent is extended or adjusted under 35 U.S.C. 154(b) by 199 days.

(21) Appl. No.: 12/436,141

(22) Filed: May 6, 2009

(65) Prior Publication Data
US 2010/0045979 A1      Feb. 25, 2010

(30) Foreign Application Priority Data

Aug. 20, 2008   (CN) .......................... 2008 1 0304074

(51) Int. Cl.
*G01N 21/25* (2006.01)
(52) U.S. Cl. ....................................................... 356/402
(58) Field of Classification Search .................... 356/402
See application file for complete search history.

(56) References Cited

U.S. PATENT DOCUMENTS

| | | | |
|---|---|---|---|
| 2004/0033936 A1* | 2/2004 | Wulfert et al. | 514/2 |
| 2007/0029527 A1* | 2/2007 | Mills et al. | 252/408.1 |
| 2010/0044320 A1* | 2/2010 | Weber et al. | 210/749 |
| 2010/0182590 A1* | 7/2010 | Neumann et al. | 356/51 |

FOREIGN PATENT DOCUMENTS

WO   WO 2006/070554    * 7/2006

\* cited by examiner

*Primary Examiner* — Kara E Geisel
(74) *Attorney, Agent, or Firm* — Raymond J. Chew

(57) ABSTRACT

A photocatalysis testing device includes a reaction chamber, a light source, and a spectrophotometer. Reactants including a methylene blue (MB) solution and a photocatalyst can be added to the reaction chamber and illuminated by the light source. Color vanishing rate of the MB solution can be measured by the spectrophotometer. Further, the photocatalysis testing device also includes a light-tight chamber and a temperature stabilizer. The reaction chamber and the light source are received in the light-tight chamber to avoid ambient light effecting on the photocatalysis test. The spectrophotometer is positioned outside the light-tight chamber and optically coupled to the reaction chamber. The temperature stabilizer is configured for stabilizing temperature of the MB solution.

9 Claims, 1 Drawing Sheet

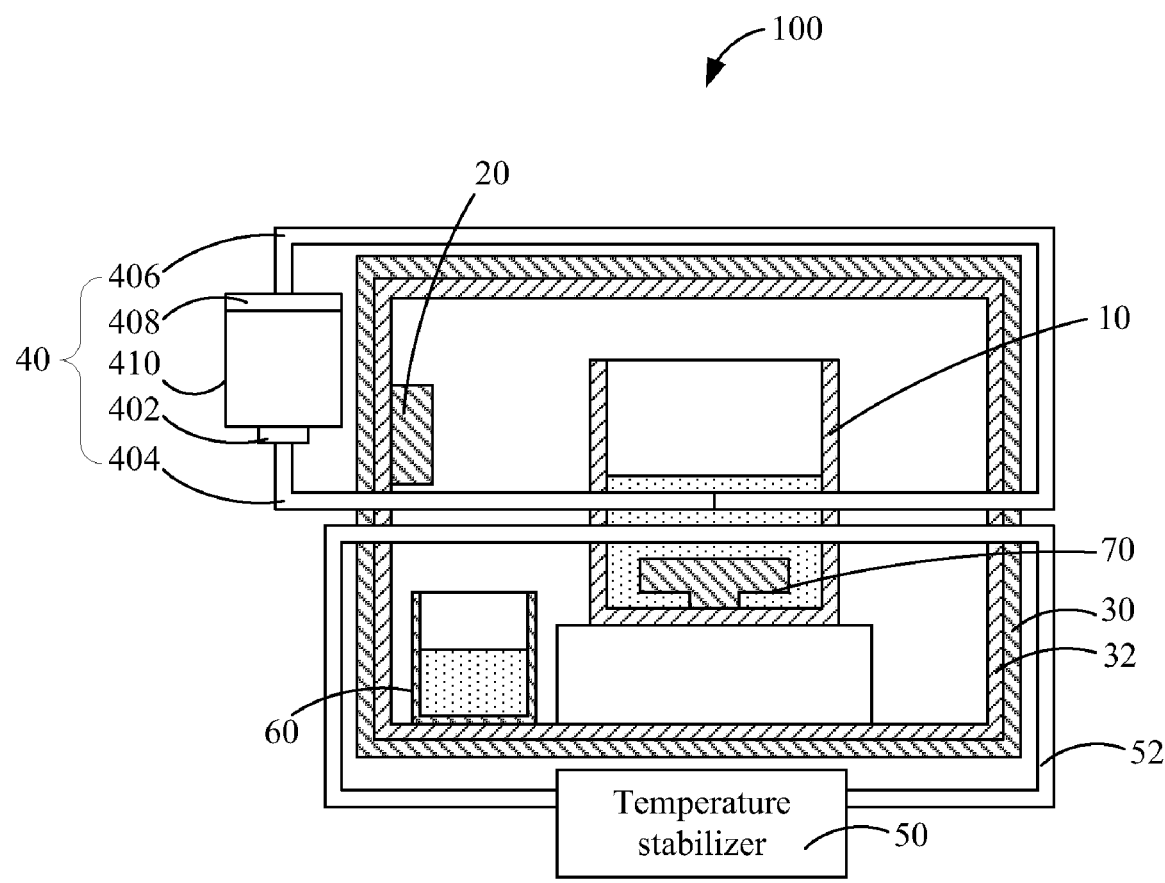

PHOTOCATALYSIS TESTING DEVICE

BACKGROUND

1. Technical Field

The present disclosure relates to testing device and, particularly, to a photocatalysis testing device.

2. Description of Related Art

Photocatalysts have excellent sterilizing, deodorizing, and anti-fouling properties and therefore are widely used in various applications. Commonly, before practical use, a photocatalysis test is required and carried out to measure photocatalytic activity of a photocatalyst to determine whether the photocatalyst is suitable for the applications.

In a current photocatalysis test, the photocatalyst is added to a methylene blue (MB) solution and illuminated by an ultraviolet (UV) light source to excite electrons thereof to a higher energy level where they can interact with MB solution. As interacted with the excited electrons, MB molecules dissolved in the MB solution degrades, causing blue color of the MB solution to vanish.

In principle, the color vanishing rate of the MB solution is a function of the degradation rate of the MB molecule and the evaporation rate of the MB solution. The color vanishing rate of the MB solution can be measured by a spectrophotometer. The degradation rate of the MB molecules is a function of the illumination intensity and the photocatalytic activity of the photocatalyst. The evaporation rate of the MB solution is a function of the solution temperature.

Therefore, if the illumination intensity and the solution temperature can be measured, the photocatalytic activity of the photocatalyst can be determined. However, in the current photocatalysis test, due to many immeasurable or unstable factors including ambient light and UV light heat, the illumination intensity and the solution temperature are difficult to be accurately measured, thereby failing attempts at acquiring an accurate photocatalytic activity of the photocatalyst.

Therefore, it is desirable to provide a photocatalysis test device, which can overcome the above-mentioned problems.

BRIEF DESCRIPTION OF THE DRAWINGS

The FIGURE is a schematic, cross-sectional view of a photocatalysis testing device in accordance with an exemplary embodiment.

DETAILED DESCRIPTION

Referring to the FIGURE, a photocatalysis testing device 100, according to an exemplary embodiment, includes a reaction chamber 10, a light source 20, a light-tight chamber 30, a spectrophotometer 40, and a temperature stabilizer 50.

The reaction chamber 10 is configured for containing reactants (not labeled). The reactants include a MB solution and a photocatalyst such as titanium dioxide, zinc oxide, tin oxide, zirconium dioxide, or cadmium sulfide. In this embodiment, the reaction chamber 10 is a beaker. The photocatalyst is titanium dioxide powder.

The light source 20 such as a UV lamp is configured for illuminating the reactants.

The reaction chamber 10 and the light source 20 are received in the light-tight chamber 30. The light-tight chamber 30 is configured for shielding the reaction chamber 10 from being illuminated by ambient light to eliminate or at least reduce influence of the ambient light on the photocatalysis test. Thereby, immeasurable ambient light factor is eliminated. In this embodiment, the light-tight chamber 30 is a cuboid made from light-tight material. Opportunely, the light-tight chamber 30 includes a reflective layer 32 formed, e.g., coated, on the inner surface of the light-tight chamber 30 to guide UV light generated by the light source 20 to the reaction chamber 10.

The spectrophotometer 40 is configured for measuring color vanishing rate of the MB solution and includes an emitter 402, a first fiber 404, a second fiber 406, a sensor 408, and a reader 410. The emitter 402 is positioned outside of the light-tight chamber 30 and configured for emitting carrier light. The first fiber 404 connects the emitter 402 and the reaction chamber 10 and is configured for guiding the carrier light from the emitter 402 to the reaction chamber 10. The second fiber 406 connects the reaction chamber 10 and the sensor 408 and is configured for guiding the carrier light from the reaction chamber 10 to the sensor 408. The sensor 408, such as a charge-coupled device or a complementary metal-oxide semiconductor (CMOS), is positioned outside of the light-tight chamber 30 and is configured for sensing color of the carrier light. The reader 410 is positioned outside of the light-tight chamber 30 and is configured for calculating the color vanishing rate of the MB solution using the sensed color of the carrier light, according to Lambert-Beer's law, and presenting the calculated color vanishing rate to users.

The temperature stabilizer 50 is configured for stabilizing the solution temperature. Thereby, unstable solution temperature factor can be avoided. In this embodiment, the temperature stabilizer 50 is positioned outside of the light-tight chamber 30 and thermally coupled to the reaction chamber 10 using a heat pipe 52.

Beneficially, the photocatalysis testing device 100 further includes a stirrer 60 and a water container 70. The stirrer 60 is received in the light-tight chamber 30 and configured for stirring the reactants. The water container 70 is also received in the light-tight chamber 30 and configured for increasing water pressure in the light-tight chamber 30 to reduce evaporation rate of the MB solution.

While the disclosure has been described by way of example and in terms of preferred embodiment, it is to be understood that the disclosure is not limited thereto. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A photocatalytic activity testing device comprising:
    a reaction chamber for containing a methylene blue solution and a photocatalyst;
    a light source for illuminating the methylene blue solution and the photocatalyst contained in the reaction chamber;
    a light-tight chamber, the reaction chamber and the light source being received in the light-tight chamber;
    a spectrophotometer comprising:
        an emitter positioned outside the light-tight chamber and configured for emitting carrier light;
        a first fiber interconnecting the emitter and the reaction chamber and configured for guiding the carrier light from the emitter to the reaction chamber;
        a second fiber;
        a sensor positioned outside the light-tight chamber, the second fiber interconnecting the reaction chamber and the sensor and being configured for guiding the carrier light from the reaction chamber to the sensor, the sensor being configured for sensing color of the carrier light from the reaction chamber; and a reader configured for calculating color vanishing rate of the methylene blue solution using the sensed color, according to Lambert-Beer's law and presenting the calculated color vanishing rate of the methylene blue solution to users; and a temperature stabilizer configured for stabilizing temperature of the methylene blue solution.

2. The photocatalysis testing device as claimed in claim 1, wherein the reaction chamber is light-permeable.

3. The photocatalysis testing device as claimed in claim 1, wherein the light source is an ultraviolet lamp.

4. The photocatalysis testing device as claimed in claim 1, wherein the light-tight chamber is a cuboid.

5. The photocatalysis testing device as claimed in claim 1, wherein the light-tight chamber comprises a reflective film formed on the inner surface of the light-tight chamber.

6. The photocatalysis testing device as claimed in claim 1, wherein the sensor is selected from the group consisting of a charge-coupled device and a complementary metal-oxide semiconductor.

7. The photocatalysis testing device as claimed in claim 1, wherein the temperature stabilizer is positioned outside the light-tight chamber, the photocatalysis testing device further comprising a heat pipe for thermally coupling the temperature stabilizer to the reaction chamber.

8. The photocatalysis testing device as claimed in claim 1, further comprising a stirrer, the stirrer being received in the light-tight chamber and configured for stirring the methylene blue solution.

9. The photocatalysis testing device as claimed in claim 1, further comprising a water container, the water container being received in the light-tight chamber and for increasing water pressure in the light-tight chamber.

* * * * *